(12) United States Patent
Ogawa et al.

(10) Patent No.: US 7,044,986 B2
(45) Date of Patent: May 16, 2006

(54) HAIR DYE COMPOSITIONS

(75) Inventors: Masahiko Ogawa, Tokyo (JP); Takashi Hori, Tokyo (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 10/614,811

(22) Filed: Jul. 9, 2003

(65) Prior Publication Data

US 2004/0010865 A1 Jan. 22, 2004

Related U.S. Application Data

(63) Continuation of application No. 09/722,483, filed on Nov. 28, 2000, now abandoned.

(30) Foreign Application Priority Data

Dec. 2, 1999 (JP) ................................. 11-343352

(51) Int. Cl.
*A61K 7/13* (2006.01)

(52) U.S. Cl. ...................... 8/405; 8/406; 8/435; 8/441; 8/543; 8/594; 8/619; 8/623; 8/620; 132/202; 132/208

(58) Field of Classification Search .................... 8/401, 8/405, 406, 618, 619, 620, 623, 435, 441, 8/543, 594; 424/401; 132/202, 208
See application file for complete search history.

(56) References Cited

U.S. PATENT DOCUMENTS

| | | | |
|---|---|---|---|
| 5,100,436 A | 3/1992 | Wenke | 8/408 |
| 5,219,562 A | 6/1993 | Fujiu et al. | 424/71 |
| 5,273,550 A | 12/1993 | Prota et al. | 8/405 |
| 5,368,610 A * | 11/1994 | Chan et al. | 8/406 |
| 5,817,155 A | 10/1998 | Yasuda et al. | 8/406 |
| 6,071,504 A | 6/2000 | Kawai et al. | 424/70.12 |
| 6,187,058 B1 * | 2/2001 | Massoni | 8/406 |
| 6,217,889 B1 | 4/2001 | Lorenzi et al. | 424/401 |
| 6,267,975 B1 | 7/2001 | Smith, III et al. | 424/401 |

FOREIGN PATENT DOCUMENTS

| | | |
|---|---|---|
| FR | 1 514 179 | 2/1968 |
| JP | 62-26212 | 2/1967 |
| JP | 53-72836 | 6/1978 |
| JP | 60-155108 | 8/1985 |
| JP | 61-130209 | 6/1986 |
| JP | 1-165514 | 6/1989 |
| JP | 4-312514 | 11/1992 |
| JP | 5-97637 | 4/1993 |
| JP | 5-124940 | 5/1993 |
| JP | 6-87727 | 3/1994 |
| JP | 6-62396 | 8/1994 |
| JP | 6-65643 | 8/1994 |
| JP | 7-2637 | 1/1995 |
| JP | 7-149618 | 6/1995 |
| JP | 7-228514 | 8/1995 |
| JP | 7-233035 | 9/1995 |
| JP | 8-40853 | 2/1996 |
| JP | 10-67624 | 3/1998 |
| JP | 10-279591 | 10/1998 |
| JP | 11-180837 | 7/1999 |
| JP | 11-343219 | 12/1999 |
| JP | 2001-158722 | 11/2001 |

OTHER PUBLICATIONS

Yakuji Nippo, Ltd., "Raw Material Specifications for Quasi-Drugs", (ISBN4-8408-0221-1, Printed by K.K. Yobunsha, First print published Jun. 15, 1991, Material 2 (excerpt translation).
Science of Wave, (1994), pp. 197-205.
Cosmetic Science Guidebook, (1979), p. 116.
Nikkei Snagyo Shinbun, May 1, 2000, Hair dyeing agent with little odor.

* cited by examiner

*Primary Examiner*—Eisa Elhilo
(74) *Attorney, Agent, or Firm*—Oblon, Spivak, McClelland, Maier & Neustadt, P.C.

(57) ABSTRACT

Hair dye compositions comprise (A) ammonia or an ammonium salt, (B) a carbonate (other than an ammonium salt), (C) a transition metal salt, and (D) a chelating agent, and have a pH of from 8.5 to 12. They do not give off an intensely irritating odor and have low irritating property, can change hair into a lighter tone in a short time or can dye hair well in a color ranging from a light color to a deep color, and moreover, assure good retention of the thus-obtained tone or color.

12 Claims, No Drawings

HAIR DYE COMPOSITIONS

TECHNICAL FIELD

This invention relates to hair dye compositions, each of which does not give off an intensely irritating odor and has low irritating property, can change hair into a lighter tone in a short time or can dye hair well in a color ranging from a light color to a deep color, and moreover, assures good retention of the thus-obtained tone or color.

BACKGROUND ART

In recent years, there is an increasing demand from consumers toward dyeing their hair in a lighter color than their own haircolor (starting haircolor), and many products generally called "fashion hair dyes" are available on the market.

Hair dyes, which are used for such purposes and include hair bleaches, are each composed of a first pack containing an alkali agent and a second pack containing an oxidizing agent. The alkali agent employed in the first pack has been added to heighten bleaching or dyeing effect and to obtain a wide range of colors ranging from a light color to a deep color. In particular, when one wants to change his or her hair into a tone lighter than the tone of his or her own haircolor, sufficient bleaching power is required. When a hair dye is used for such purposes, a fully sufficient amount of an alkali is therefore required. To dye hair well with good color retention, a sufficient amount of an alkali is also required.

Conventionally, ammonia has been used as an alkali agent in general. Ammonia is, however, accompanied by drawbacks that it has an intensely irritating odor and makes consumers feel unpleasant upon dyeing.

Transition metals have, therefore, been used in attempts to accelerate a reaction with an oxidizing agent and hence to heighten bleaching power or dyeing power (for example, JP 4-312514 A, JP5-124940A, JP6-87727A, and JP4-312514). These attempts, however, all require further treatment with a hair dye after hair is left over with a metal-ion-containing preparation applied thereon beforehand. They thus involves a problem of irksomeness, and moreover, they neither have sufficient dyeing ability nor assure satisfactory color retention.

It has also been attempted to incorporate transition metal ions in first packs (for example, JP 61-130209 A and JP 6-65643 B). However, such first packs are all used under neutral to weak alkaline conditions of pH 6 to pH 8.5, and accordingly, their alkali contents are not sufficient. No sufficient bleaching power is thus available from them, leading to failure in dyeing hair in a light color. These attempts also involve a problem that a dyed color does not stay long.

An object of the present invention is to provide a hair dye composition, which does not give off an intensely irritating odor and has low irritating property, can change hair into a lighter tone in a short time or can dye hair well in a color ranging from a light color to a deep color, and moreover, assures good retention of the thus-obtained tone or color.

DISCLOSURE OF THE INVENTION

The present inventors have found that combined use of ammonia or an ammonium salt, a carbonate, a transition metal salt and a chelating agent in specific proportions can provide a hair dye composition which is reduced in the irritating odor of ammonia and is free of the above-described problems.

The present invention, therefore, provides a hair dye composition comprising the following ingredients (A) to (D):

| | | |
|---|---|---|
| (A) | ammonia or an ammonium salt | 0.01 to 3 mol/kg, |
| (B) | a carbonate with a proviso that said carbonate is other than an ammonium salt | 0.001 to 1 mol/kg, |
| (C) | a transition metal salt | 0.1 to 10,000 ppm, |
| (D) | a chelating agent | | the molar ratio of (A) to (B) [(A)/(B)] being 0.1 to 5, and said hair dye composition having a pH of from 8.5 to 12.

BEST MODES FOR CARRYING OUT THE INVENTION

Preferred examples of the ammonium salt as the ingredient (A) can include ammonium chloride, ammonium sulfate, ammonium nitrate, ammonium carbonate, ammonium hydrogencarbonate, ammonium phosphate, and ammonium carbonate, among which ammonium chloride, ammonium carbonate and ammonium hydrogencarbonate are particularly preferred.

As the ingredient (A), ammonia and an ammonium salt may be used in combination, and their total content is 0.01 to 3 mol/kg in the composition according to the present invention from the standpoint of tone and color retention, with 0.1 to 1 mol/kg, especially 0.15 to 0.6 mol/kg being preferred.

Examples of the carbonate as the ingredient (B) can include carbonates and hydrogencarbonates, with the proviso that ammonia salts are excluded. Illustrative are sodium carbonate, sodium hydrogencarbonate, potassium carbonate, potassium hydrogencarbonate, guanidine carbonate, guanidine hydrogencarbonate, lithium carbonate, calcium carbonate, magnesium carbonate, and barium carbonate. Of these, potassium carbonate and guanidine carbonate are particularly preferred.

The content of the ingredient (B) is 0.001 to 1 mol/kg in the composition according to the present invention from the standpoint of bleaching performance and irritation to the scalp, with 0.01 to 0.5 mol/kg, especially 0.05 to 0.3 mol/kg being particularly preferred.

Further, the molar ratio of (A) to (B) [(A)/(B)] is 0.1 to 5 from the standpoint of irritating odor and bleaching performance, with 0.2 to 3, especially 0.3 to 1.5 being preferred.

The transition metal salt as the ingredient (C) may be a water-soluble salt of a transition metal. Illustrative of such a water-soluble salt are the hydrochlorides, sulfates, nitrates, phosphates and organic acid salts of metals such as iron, copper, zinc, cobalt, nickel, manganese, and silver. Among these, water-soluble salts of iron, for example, ferrous sulfate and ferrous chloride are particularly preferred.

The transition metal salt as the ingredient (C) is incorporated in the composition according to the present invention such that the content of transition metal ions becomes 0.1 to 10,000 ppm, with an ion content of from 1 to 100 ppm being particularly preferred.

No particular limitation is imposed on the chelating agent as the ingredient (D) insofar as it has ability to chelate metal ions in the ingredient (C) and is commonly used in cosmetic preparations. Illustrative are ethylenediaminetetraacetic acid, hydroethylethylenediaminetriacetic acid, diethylenetriaminepentaacetic acid, nitrilotriacetic acid, triethylenetetraminehexaacetic acid, phosphonic acids, tripolyphosphoric acid, ascorbic acid, citric acid, maleic acid, and salts thereof. Of these, ethylenediaminetetraacetic acid is particularly preferred.

The chelating agent as the ingredient (D) may be incorporated preferably in a proportion of from 0.01 to 10 wt.%, especially from 0.1 to 1.0 wt.% in the composition according to the present invention.

The pH of the hair dye composition according to the present invention is adjusted to 8.5 to 12, preferably 9 to 11.5, notably 10 to 11. The term "pH" as used herein means a pH value of a hair dye concentrate as measured, as is, without dilution.

The pH adjustment is effected in a manner known per se in the art by using an alkali agent or acid other than those described above. Usable examples of the alkali agent can include alkanolamines such as monoethanolamine, diethanolamine, triethanolamine, monopropanolamine, dipropanolamine, tripropanolamine, 2-amino-2-methyl-1,3-propanediol, 2-amino-2-methyl-1-propanol, and 2-amino-2-hydroxymethyl-1,3-propanediol; and guanidium salts such as guanidine hydrochloride, guanidine sulfate, guanidine nitrate, guanidine phosphate, guanidine thiophosphate, guanidine borate, guanidine sulfamate, and the guanidine salts of organic acids.

Here, combined use of an alkanolamine (ingredient E) as the alkali agent is preferred for heightening dyeing power or bleaching agent.

The hair dye composition according to the present invention may contain oxidation dye intermediate or as in the case of so-called "hair bleaches", may not contain such an oxidation dye intermediate. It should be noted that they are both encompassed in the present invention. When the oxidation dye intermediate is used, it is added to a first dye pack. As the oxidative dye intermediate, a color-developing substance and a coupling substance are added.

No particular limitation is imposed on the color-developing substance insofar as it is commonly used in oxidative hair dyes. Examples of the color-developing substance can include p-phenylenediamines having one or more $H_2N$-groups, RHN-groups or $(R)_2N$-groups in which each R represents an alkyl or hydroxyalkyl group having 1 to 4 carbon atoms, such as p-phenylenediamine, p-toluylenediamine, N-methyl-p-phenylene-diamine, N,N-dimethyl-p-phenylenediamine, N,N-diethyl-2-methyl-p-phenylenediamine, N-ethyl-N-(hydroxyethyl)-p-phenylenediamine, chloro-p-phenylenediamine, 2-(2'-hydroxyethylamino)-5-aminotoluene, N,N-bis-(2-hydroxyethyl)-p-phenylenediamine, methoxy-p-phenylenediamine, 2,6-dichloro-p-phenylenediamine, 2-chloro-6-bromo-p-phenylenediamine, 2-chloro-6-methyl-p-phenylenediamine, 6-methoxy-3-methyl-p-phenylenediamine, 2,5-diaminoanisole, N-(2-hydroxypropyl)-p-phenylenediamine, and N-2-methoxyethyl-p-phenylenediamine; and p-aminophenols, o-aminophenols and o-phenylenediamines, such as p-aminophenol, 2-methyl-4-aminophenol, 3-methyl-4-aminophenol, 2-chloro-4-aminophenol, 3-chloro-4-aminophenol, 2,6-dimethyl-4-aminophenol, 3,5-dimethyl-4-aminophenol, 2,3-dimethyl-4-aminophenol, 2,5-dimethyl-4-aminophenol, and 2,4-diaminophenol, 5-aminosalicylic acid.

On the other hand, examples of the coupling substance can include α-naphthol, o-cresol, m-cresol, 2,6-dimethylphenol, 2,5-dimethylphenol, 3,4-dimethylphenol, 3,5-dimethylphenol, benzcatechin, pyrogallol, 1,5-dihydroxynaphthalene, 1,7-dihydroxynaphthalene, 5-amino-2-methylphenol, 5-(2'-hydroxyethylamino)-4-methoxyphenol, hydroquinone, 2,4-diaminoanisole, m-toluylenediamine, 4-aminophenol, resorcin, resorcin monomethyl ether, m-phenylenediamine, 1-phenyl-3-methyl-5-pyrazolone, 1-phenyl-3-amino-5-pyrazolone, 1-phenyl-3,5-diketo-pyrazolidine, 1-methyl-7-dimethylamino-4-hydroxy-2-quinolone, m-aminophenol, 4-chlororesorcin, 2-methylresorcin, 2,4-diaminophenoxyethanol, 2,6-diaminopyridine, 3,5-diaminotrifluoromethylbenzene, 2,4-diaminofluorobenzene, 3,5-diaminofluorobenzene, 2,4-diamino-6-hydroxypyrimidine, 2,4,6-triaminopyrimidine, 2-amino-4,6-dihydroxypyrimidine, 4-amino-2,6-dihydroxypyrimidine, and 4,6-diamino-2-hydroxypyrimidine.

These color-developing substances may be used either singly or in combination. Likewise, these coupling substances may also be used either singly or in combination. It is preferred to incorporate such color-developing substance or substances and such coupling substance or substances, each, in a total proportion of from 0.01 to 20 wt. %, especially from 0.5 to 10 wt. % in the hair dye composition according to the present invention. Further, a direct dye may also be incorporated in the first dye pack to additionally tune the color.

As also described above, the composition according to the present invention may be formulated as a first bleach pack without adding such an oxidation dye intermediate.

When formulated as a first dye pack or a first bleach pack, it is preferred to mix it with an oxidizing agent upon use. Illustrative of the oxidizing agent are hydrogen peroxide, an adduct of hydrogen peroxide with urea, melamine or sodium borate, and a mixture of such a hydrogen peroxide adduct and potassium peroxidedisulfate.

Upon use, the first dye pack or the first bleach pack is generally mixed with a liquid or cream-like oxidizing agent composition (second pack), which contains about 6 wt. % of hydrogen peroxide, at 1:1 to 1:3 (by weight ratio), the mixture so prepared is applied to hair at a temperature of from 15 to 40° C., and after the hair is left over for 1 to 50 minutes, preferably from 10 to 30 minutes, the mixture is washed off.

It is preferred to additionally incorporate an antioxidant such as a nitrite or a salt of thioglycolic acid in the composition according to the present invention.

It is also possible to add, as needed, ingredients employed in general cosmetic preparations, for example, viscosity/gel strength modifiers, oils and fats, waxes, hydrocarbons, polyhydric alcohols, esters, amides, silicone derivatives, cationic surfactants, anionic surfactants, amphoteric surfactants, nonionic surfactants, nonionic polymers, anionic polymers, amphoteric polymers, protein derivatives, amino acids, preservatives, stabilizers, plant extracts, crude drug extracts, vitamins, colorants, perfumes, pigments, ultraviolet absorbers and the like.

The composition according to the present invention can be prepared in a manner known per se in the art, and as its preparation form, can be formulated into a clear lotion, an emulsion, a cream, a gel, a paste, or a mouss.

EXAMPLE 1 AND COMPARATIVE EXAMPLES 1–2.

In each of these example and comparative examples, a first dye pack of the corresponding formulation shown in Table 1 and a second pack of the formulation presented in Table 2 were prepared, and were ranked as to irritating odor, irritation to the scalp, dyeability, color retention and lightness. The results are also shown in Table 1.

(Ranking Methods)

(1) Irritating Odor

The second pack was added to and mixed with the first pack in equal amounts (by weight). An odor of the mixture was ranked in accordance with the following standard:
- A: No substantial irritating odor was felt.
- B: A slight irritating odor was felt.
- C: A strong irritating odor was felt.

(2) Irritation to Scalp

An equiamount mixture of the first pack and the second pack was applied to the scalp, and irritation to the scalp was then ranked in accordance with the following standard:
- A: No substantial irritation was felt.
- B: Slight irritation was felt.
- C: Strong irritation was felt.

(3) Dyeability

An equiamount mixture of the first pack and the second pack was applied to a white tress, and after the white tress was allowed to stand at 30° C. for 15 minutes, the white tress was rinsed and shampooed and then dried. The dyeability of the tress was visually ranked in accordance with the following standard:
- A: Dyed even and well.
- B: Not dyed well, or dyed somewhat uneven.
- C: Practically not dyed, or dyed uneven.

(4) Color Retention

After the white tress dyed in the above test (3) was repeatedly washed 20 times with a commercial shampoo, the white tress was visually ranked in accordance with the following standard:
- A: No substantial difference was observed from the tress before the shampooing.
- B: Some fading was observed in comparison with the tress before the shampooing.
- C: Substantial fading was observed in comparison with the tress before the shampooing.

(5) Lightness

Using a black tress, dyeing was performed in a similar manner as in the test (3). The lightness of the tress was visually ranked in accordance with the following standard:
- A: Dyed in a natural, light, chestnut color.
- B: Dyed in a somewhat dark brown color.
- C: Dyed in a dark black-brown color.

TABLE 1

| Ingredient (wt. %) | Ex. 1 | Comp. Ex. 1 | Comp. Ex. 2 |
| --- | --- | --- | --- |
| Aqueous ammonia (28%) | 0.5 | 0.5 | 0.5 |
| Ammonium chloride | 0.5 | 0.5 | 0.5 |
| Ferrous sulfate | 15 ppm | 15 ppm | — |
| Tetrasodium ethylenediaminetetraacetate | 0.1 | — | 0.1 |
| Monoethanolamine | 3.5 | 3.5 | 3.5 |
| Potassium carbonate | 2.5 | 2.5 | 2.5 |
| Toluene-2,5-diamine | 1.0 | 1.0 | 1.0 |
| Resorcin | 0.4 | 0.4 | 0.4 |
| Metaaminophenol | 0.2 | 0.2 | 0.2 |
| Cetanol | 6 | 6 | 6 |
| Octyldodecanol | 1 | 1 | 1 |
| Polyoxyethylene (40) cetyl ether | 3.0 | 3.0 | 3.0 |
| Polyoxyethylene (2) cetyl ether | 3.5 | 3.5 | 3.5 |
| Liquid paraffin | 1.0 | 1.0 | 1.0 |
| Propylene glycol | 6.0 | 6.0 | 6.0 |
| Sodium sulfite | 0.5 | 0.5 | 0.5 |
| Ascorbic acid | 0.5 | 0.5 | 0.5 |
| Perfume | 0.3 | 0.3 | 0.3 |
| Hydrochloric acid | Sufficient to adjust pH to 10.5 | | |
| Water | Balance | | |
| Content of ingredient (A) (mol/kg) | 0.175 | 0.175 | 0.175 |
| Content of ingredient (B) (mol/kg) | 0.181 | 0.181 | 0.181 |
| (A)/(B) (molar ratio) | 0.967 | 0.967 | 0.967 |
| Ranked Property — Irritating odor | A | A | A |
| Irritation to the scalp | A | A | A |
| Dyeability | A | B | B |
| Color retention | A | C | C |
| Lightness | A | C | C |

TABLE 2

| Ingredient | Added amount (wt. %) |
| --- | --- |
| Hydrogen peroxide (35%) | 17.1 |
| Methylparaben | 0.1 |
| Phosphoric acid | Sufficient to adjust pH to 3.5 |
| Water | Balance |

EXAMPLE 2

A first dye pack of the formulation shown in Table 3 was prepared in a manner known per se in the art.

To the thus-obtained first pack, a second pack of the formulation shown above in Table 2 was added in an equal amount (by weight). In a manner similar to Example 1, the resulting mixture was ranked as to irritating odor, irritation to the scalp, dyeability, color retention and lightness. Those properties were all ranked "A".

TABLE 3

| Ingredient | Added amount (wt. %) |
| --- | --- |
| Aqueous ammonia (28%) | 1.0 |
| Ammonium hydrogencarbonate | 1.3 |
| Ferrous sulfate | 20 ppm |
| Tetrasodium ethylenediaminetetraacetate | 0.2 |
| Monoethanolamine | 3.0 |
| Monoethanolamine hydrochloride solution (60%) | 1.2 |
| Potassium carbonate | 2.0 |
| Toluene-2,5-diamine | 1.5 |
| Resorcin | 0.6 |
| Metaaminophenol | 0.3 |
| Oleic acid | 10.0 |
| Diethanolamide oleate | 8.0 |
| Polyoxyethylene (20) octyldodecyl ether | 10.0 |
| Ethanol | 15.0 |
| Propylene glycol | 10.0 |
| Sodium sulfite | 0.5 |
| Ascorbic acid | 0.5 |
| Perfume | 0.3 |
| Hydrochloric acid | Sufficient to adjust pH to 11.0 |
| Water | Balance |
| Content of ingredient (A) (mol/kg) | 0.33 |
| Content of ingredient (B) (mol/kg) | 0.145 |
| (A)/(B) (molar ratio) | 2.28 |

EXAMPLE 3

A first bleach pack of the formulation shown in Table 4 was prepared in a manner known per se in the art.

To the thus-obtained first pack, a second pack of the formulation shown above in Table 2 was added in an equal amount (by weight). In a manner similar to Example 1, the resulting mixture was ranked as to irritating odor, irritation to the scalp, and lightness. Those properties were all ranked "A".

TABLE 4

| Ingredient | Added amount (wt. %) |
| --- | --- |
| Aqueous ammonia (28%) | 2.5 |
| Guanidine carbonate | 2.0 |
| Ferrous sulfate | 30 ppm |
| Tetrasodium ethylenediaminetetraacetate | 0.3 |
| Monoethanolamine | 2.5 |
| Oleic acid | 10.0 |
| Diethanolamide oleate | 8.0 |
| Polyoxyethylene (20) octyldodecyl ether | 10.0 |
| Ethanol | 15.0 |
| Propylene glycol | 10.0 |
| Sodium sulfite | 0.5 |
| Ascorbic acid | 0.5 |
| Perfume | 0.3 |
| Sodium hydrogencarbonate | Sufficient to adjust pH to 11.0 |
| Water | Balance |
| Content of ingredient (A) (mol/kg) | 0.412 |
| Content of ingredient (B) (mol/kg) | 0.165 |
| (A)/(B) (molar ratio) | 2.50 |

INDUSTRIAL APPLICABILITY

The hair dye compositions according to the present invention do not give off an intensely irritating odor and have low irritating property, can change hair into a lighter tone in a short time or can dye hair well in a color ranging from a light color to a deep color, and moreover, assures good retention of the thus-obtained tone or color. They are suitable as first dye packs or first bleach packs.

The invention claimed is:

1. A method of dyeing the hair, comprising:
   mixing a first pack formulation and a second pack formulation, said first pack formulation comprising the following ingredients (A) to (D):

| | | |
| --- | --- | --- |
| (A) | ammonia or an ammonium salt | 0.01 to 3 mol/kg, |
| (B) | a carbonate with a proviso that said carbonate is other than an ammonium salt | 0.001 to 1 mol/kg, |
| (C) | a transition metal salt | 0.1 to 10,000 ppm, |
| (D) | a chelating agent | | wherein the molar ratio of (A) to (B) ranges from 0.1 to 5, and
the first pack formulation has a pH ranging from 8.5 to 12; and said second pack comprising an acidic hydrogen peroxide solution as an oxidizing agent;
   applying the mixed first and second pack formulations to the hair;
   permitting the applied mixed formulation to dye the hair; and then
   removing the applied mixed formulation from the hair.

2. The method of dyeing hair of claim 1, wherein the second pack formulation contains about 6 wt% hydrogen peroxide.

3. The method of dyeing hair of claim 1, wherein the hair is dyed at a temperature ranging from about 15 to 40° C. for about 1 to 50 minutes.

4. The method of dyeing hair of claim 3, wherein the hair is dyed for about 10 to 30 minutes.

5. The method of dyeing hair of claim 1, wherein the applied formulation is removed from the hair by washing the hair.

6. The method of dyeing hair of claim 1, wherein the content of said ingredient (D) in the first pack formulation is 0.01 to 10 wt% based on said composition.

7. The method of dyeing hair of claim 1, wherein said water soluble salt of iron is ferrous sulfate or ferrous chloride.

8. The method of dyeing hair of claim 1, wherein the chelating agent (D) is ethylenediaminetetraacetic acid, hydroyethylethylenediaminetriacetic acid, diethylenetriaminepentaacetic acid, nitrilotriacetic acid, triethylenetetraminehexaacetic acid, a phosphonic acid, tripolyphosphoric acid, ascorbic acid, citric acid, maleic acid or salts thereof.

9. The method of dyeing hair of claim 1, wherein said carbonate (B) of the first pack formulation is sodium carbonate, sodium hydrogencarbonate, potassium carbonate, potassium hydrogencarbonate, guanidine carbonate, guanidine hydrogencarbonate, lithium carbonate, calcium carbonate, magnesium carbonate or barium carbonate.

10. The method of dyeing hair of claim 1, wherein said pH ranges from 9 to 11.5.

11. The method of dyeing hair of claim 1, wherein the amount of said carbonate in the composition ranges from 0.01 to 0.5 mol/kg.

12. The method of dyeing hair of claim 1, wherein said molar ratio of (A) to (B) ranges from 0.2 to 3.

* * * * *

UNITED STATES PATENT AND TRADEMARK OFFICE
CERTIFICATE OF CORRECTION

PATENT NO.       : 7,044,986 B2  
APPLICATION NO.  : 10/614811  
DATED            : May 16, 2006  
INVENTOR(S)      : Masahiko Ogawa et al.

Page 1 of 1

It is certified that error appears in the above-identified patent and that said Letters Patent is hereby corrected as shown below:

Column 7, line 51, "(A) ammonia or an ammonium salt   0.01 to 3 mol/kg," should read
--(A) ammonia or an ammonium salt                     0.1 to 1 mol/kg, --.

Column 8, line 3, "(C) a transition metal salt        0.1 to 10,000 ppm," should read
-- (C) a water soluble salt of iron,                  0.1 to 10,000 ppm, --.

Signed and Sealed this

Fifth Day of September, 2006

JON W. DUDAS  
*Director of the United States Patent and Trademark Office*